United States Patent
Shih et al.

(10) Patent No.: US 9,877,980 B2
(45) Date of Patent: Jan. 30, 2018

(54) METHOD AND COMPOSITION FOR TREATMENT OR PREVENTION OF TYPE 2 DIABETES AND HYPERLIPIDEMIA

(71) Applicant: Chun-Ching Shih, Taichung (TW)

(72) Inventors: Chun-Ching Shih, Taichung (TW); Jin-Bin Wu, Taichung (TW); Jia-Ying Jian, Taichung (TW); Cheng-Hsiu Lin, Taichung (TW); Hui-Ya Ho, Taichung (TW)

(73) Assignee: Chun-Ching Shih, Taichung (TW)

( * ) Notice: Subject to any disclaimer, the term of this patent is extended or adjusted under 35 U.S.C. 154(b) by 0 days.

(21) Appl. No.: 15/289,381

(22) Filed: Oct. 10, 2016

(65) Prior Publication Data

US 2017/0290851 A1    Oct. 12, 2017

(30) Foreign Application Priority Data

Apr. 12, 2016   (TW) .............................. 105111297 A

(51) Int. Cl.
*A61K 31/7048* (2006.01)
(52) U.S. Cl.
CPC ................................. *A61K 31/7048* (2013.01)
(58) Field of Classification Search
None
See application file for complete search history.

(56) References Cited

PUBLICATIONS

Cui et al., Chemical & Pharmaceutical Bulletin, 38(9), 1990, 2620-2622.*
Chun-Ching Shih et al., "(−)-Epicatechin-3-O-β-D-allopyranoside from Davallia formosana, Prevents Diabetes and Hyperlipidemia by Regulation of GlucoseTransporter 4 and AMP-Activated Protein Kinase Phosphorylation in High-Fat-Fed Mice", Int. J. Mol. Sci. 2015, 16.

* cited by examiner

*Primary Examiner* — Travis C McIntosh, III
(74) *Attorney, Agent, or Firm* — Wang Law Firm, Inc.

(57) ABSTRACT

The present invention provides a method of treating or preventing type 2 diabetes and hyperlipidemia in a subject in need thereof, comprising administrating to the subject a therapeutically effective amount of a compound of formula I. The present invention also provides a pharmaceutical composition for treatment or prevention of type 2 diabetes and hyperlipidemia, comprising a compound of formula I and a pharmaceutically acceptable carrier. Through down-regulation of PEPCK, G6Pase, 11β-HSD1, DGAT2, and GPAT, up-regulation of PPARα and adiponectin, and promotion of membrane GLUT4 expression and phosphorylation of AMPK and Akt, the compound of formula I of the present invention exerts antidiabetic and antihyperlipidemic effects, including reduced weight of visceral fat, decreased blood levels of triglycerides, free fatty acids, glucose, insulin, and leptin as well as decreased hepatic levels of total lipid and triacylglycerol. The compound of formula I also inhibits adipocyte hypertrophy and hepatic ballooning.

15 Claims, 11 Drawing Sheets

```
                          SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ctacaacttc ggcaaatacc                                                 20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tccagatacc tgtcgatctc                                                 20

<210> SEQ ID NO 3
<211> LENGTH: 22
<212> TYPE: DNA
<213> ORGANISM: Artificial Sequence
<220> FEATURE:
<223> OTHER INFORMATION: PCR primer

<400> SEQUENCE: 3
gaacaactaa agcctctgaa ac                                              22

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
ttgctcgata cataaaacac tc                                              22

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
aagcagagca atggcagcat                                                 20

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
gagcaatcat aggctgggtc a                                               21
```

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
tcttctacaa ccaacagaat ca                                          22

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
gtatcatggt agagaaggaa gc                                          22

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
cctgagatta accagccttt                                             20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
aggacctact ctcattgctg                                             20

<210> SEQ ID NO 11
<211> LENGTH: 18
<212> TYPE: DNA
<213> ORGANISM: Artificial Sequence
<220> FEATURE:
<223> OTHER INFORMATION: PCR primer

<400> SEQUENCE: 11
cagtcctgaa taagaggt                                               18

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
tggacaaaga tggcagcaga                                             20

<210> SEQ ID NO 13
<211> LENGTH: 20
<212> TYPE: DNA
<213> ORGANISM: Artificial Sequence
<220> FEATURE:
<223> OTHER INFORMATION: PCR primer

```
<400> SEQUENCE: 13
tgtgtccgtc gtggatctga                                          20

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
cctgcttcac caccttcttg a                                        21
```

METHOD AND COMPOSITION FOR TREATMENT OR PREVENTION OF TYPE 2 DIABETES AND HYPERLIPIDEMIA

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "1424-P60017_Sequence_Listing.txt", created Oct. 10, 2016, file size of 2720 bytes, is hereby incorporated by reference.

CROSS-REFERENCE TO RELATED APPLICATION

This application claims priority of Taiwan patent application No. 105111297, filed on Apr. 12, 2016, the content of which is incorporated herein in its entirety by reference.

BACKGROUND OF THE INVENTION

1. Field of the Invention

The present invention relates to a method and a pharmaceutical composition for treatment or prevention of type 2 diabetes and hyperlipidemia. Particularly, the present invention relates to a method and a pharmaceutical composition for treatment or prevention of type 2 diabetes and hyperlipidemia with (−)-epicatechin-3-O-β-D-allopyranoside.

2. The Prior Arts

The population of diabetes mellitus (DM) will reach 300 million by 2025 and raise a huge public health issue. Type 2 diabetes mellitus accounts for over 90% diabetes cases and causes high glucose levels in blood due to enhanced liver glucose production or insulin resistance, which is the insensitive response of peripheral tissue to insulin. Since both genetics and lifestyle play important roles in pathogenesis of type 2 diabetes, numerous therapies with different targets have been developed.

One therapeutic target for type 2 diabetes is glucose transporter type 4 (GLUT4), which plays a vital role in controlling whole body glucose homeostasis. When a meal is taken, insulin is secreted and followed by stimulating glucose transport into cells. In response to insulin and other stimuli, GLUT4 has been shown to acutely redistribute from intracellular disposition to the plasma membrane. The up-regulation of GLUT4 expression in skeletal muscle has been observed in response to exercise in mice to affect glucose levels in blood.

Another therapeutic target for type 2 diabetes is 5' adenosine monophosphate-activated protein kinase (AMPK), which plays a key role in glucose and lipid metabolism and whose activation has favorable effects in peripheral tissue in type 2 diabetes.

One effective medication for type 2 diabetes is metformin. Metformin acts to improve blood glucose control mainly by inhibition of hepatic glucose production and increased peripheral glucose uptake. However, it causes side effects of lactic acidosis, vomiting, diarrhea, nausea, vomiting, and flatulence.

As described above, common antidiabetic drugs possess limited actions and side effects. Thus, researchers are motivated to develop new drugs with more general antidiabetic and lipid lowering effects. For development of novel therapies with safety and efficacy to type 2 diabetes, mouse model are constructed and induced with a high-fat diet (HFD) to cause aberrant muscular glucose uptake, insulin resistance, hyperglycemia, hyperlipidemia, hyperinsulinemia, obesity, and excess circulating free fatty acids. *Davallia formosan* Hayata is also known as Gu-Sui-Bu in the herbal market of Taiwan and is employed to treat rheumatoid arthritis. The bioactive components of *Davallia formosan* are demonstrated to be davallic acid, flavan-3-ol, and proanthocyanidin allosides. However, there has been no study on the antidiabetic and antihyperlipidemic effects of *Davallia formosan*.

SUMMARY OF THE INVENTION

As a result, the present invention provides a method of treating or preventing type 2 diabetes and hyperlipidemia in a subject in need thereof, comprising administrating to the subject a therapeutically effective amount of a compound of formula I:

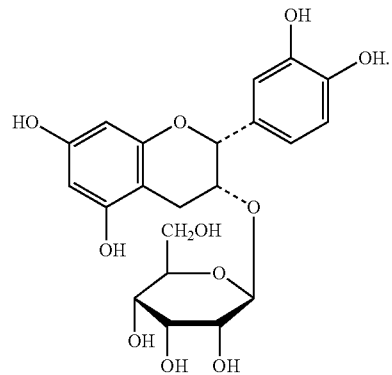

In one embodiment of the present invention, the compound of formula I reduces weights of visceral fat, epididymal white adipose tissue, and retroperitoneal white adipose tissue.

In one embodiment of the present invention, the compound of formula I reduces blood levels of glucose, insulin, triglycerides, free fatty acids, and leptin. The compound of formula I also reduces hepatic levels of total lipid and triacylglycerol. However, the compound of formula I increases a blood level of adiponectin.

In one embodiment of the present invention, the compound of formula I inhibits hypertrophy of an adipocyte and decreases hepatocellular ballooning.

In one embodiment of the present invention, the compound of formula I inhibits gene expression of phosphenolpyruvate carboxykinase (PEPCK), glucose-6-phosphatase (G6Pase), 11β hydroxysteroid dehydrogenase 1 (11-β-HSD1), diacylglycerol acyltransferase (DGAT2), and glycerol-3-phosphate-acyltransferase (GPAT) in liver, whereas the compound of formula I enhances gene expression of peroxisome proliferator-activated receptor α (PPARα) and adiponectin in liver.

In one embodiment of the present invention, the compound of formula I increases protein content of membrane glucose transporter type 4 (GLUT4) in skeletal muscle, and it also increases phosphorylation of 5' adenosine monophosphate-activated protein kinase (AMPK) and protein kinase B (Akt) in skeletal muscle and liver.

For the present invention, the therapeutically effective amount is at least 10 mg/kg/day.

In another aspect, the present invention provides a pharmaceutical composition for treatment or prevention of type 2 diabetes and hyperlipidemia, comprising a pharmaceutically acceptable carrier and a compound of formula I:

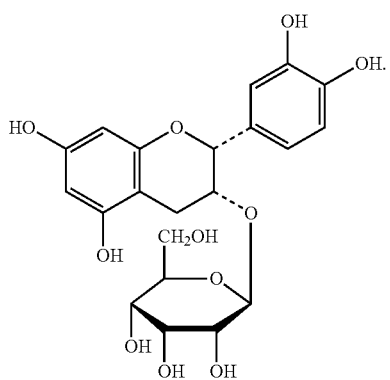

The pharmaceutical composition of the present invention may further comprise an excipient, a diluent, a medium, or combinations thereof.

The method and the pharmaceutical composition of the present invention exert antidiabetic and antihyperlipidemic effects through utilizing the compound of formula I. Therefore, the method and the pharmaceutical composition of the present invention are useful in prevention or amelioration of symptoms associated with type 2 diabetes and hyperlipidemia.

The present invention is further explained in the following drawings and examples. It is understood that the examples given below do not limit the scope of the invention, and it will be evident to those skilled in the art that modifications can be made without departing from the scope of the appended claims.

DETAILED DESCRIPTION OF THE PREFERRED EMBODIMENT

Definition

Figure 1A:
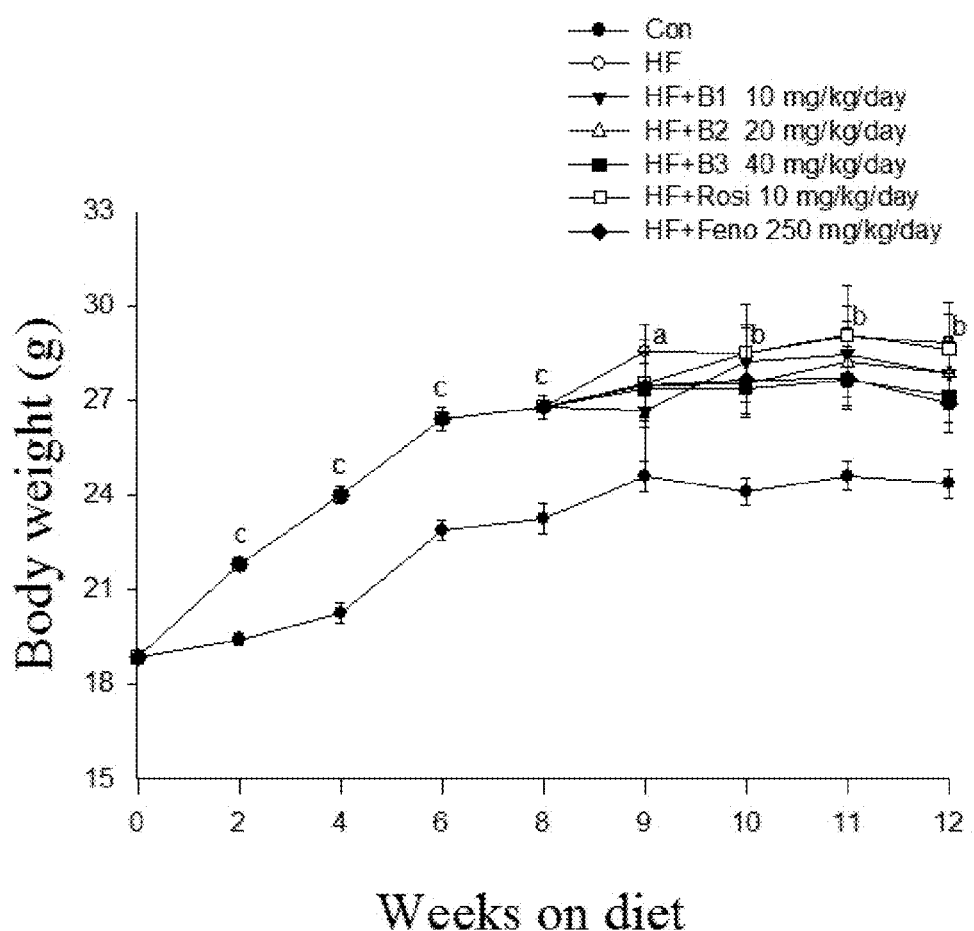
FIG. 1A shows the effect of the compound of formula I on body weight.

As used herein, the phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dosage for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts.

The term "pharmaceutically acceptable carrier" as used herein, refers to a non-toxic, solid, semi-solid or liquid filler, diluent, encapsulating material or formulation auxiliary of any type. Some examples of materials for the pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention employed a mouse model on high-fat diet (HFD) to validate the antidiabetic and antihyperlipidemic activities of the compound of formula I. To evaluate the therapeutic efficacy of the compound of formula I, a comparison of the antidiabetic and lipid-lowering effects was also performed between the compound of formula I and the marketed antidiabetic and antihyperlipidemic drugs, rosiglitazone and fenofibrate. Rosiglitazone is a member of thiazolidinediones (TZDs) used to treat type 2 diabetes and acts to enhance insulin sensitivity and protein levels of GLUT4. Fenofibrate is used to treat human hyperlipidemia and is an activator of peroxisome proliferator-activated receptor α (PPARα), which is a major regulator of genes involved in lipid metabolism, including fatty acid oxidation and lipogenesis. In addition, the ameliorating effects of the compound of formula I on adipocyte hypertrophy and hepatocellular ballooning were examined. For further understanding of the action of the compound of formula I on glucose and lipid metabolism at the molecular level, the expression levels and the phosphorylation status of specific proteins related to the pathogenesis of type 2 diabetes and hyperlipidemia were analyzed.

Materials and Methods

Preparation of the Extract of *Davallia Formosanav*

The roots and stems of *Davallia formosana*, obtained from a local market in Taichung, Taiwan, were extracted with 75% ethanol and followed by evaporation of the solvent under reduced pressure at 50° C. The yield of the extract of *D. formosana* (DFE) was 9.5 wt %. The DFE was then suspended in water, partitioned with N-butanol, and concentrated. The yield of the N-butanol fraction was 20.2 wt %.

Purification of the Compound of Formula I

The N-butanol fraction (10 g) was introduced into an HP-20 column (Diaion, NIPPON RESSUI Company, Tokyo, Japan) and eluted with water and methanol. Eight fractions were obtained (fractions 1-8). Fraction 6 (230 mg) was further purified by high performance liquid chromatography (HPLC; Shimadzu CL-8A, Kyoto, Japan) equipped with a preparative column (5C18-MS-II, 10 mm I.D.×250 mm) to obtain the pure compound (136 mg). The conditions for HPLC were as follows: the mobile phase was methanol-water (9:1); UV detection was performed at 270 nm.

The purified compound was analyzed by NMR (1H, 13C; Bruker ADVANCE DPX-200, Rheinstetten, Germany) and was identified as (−)-epicatechin-3-O-β-D-allopyranoside, that is, the compound of formula I:

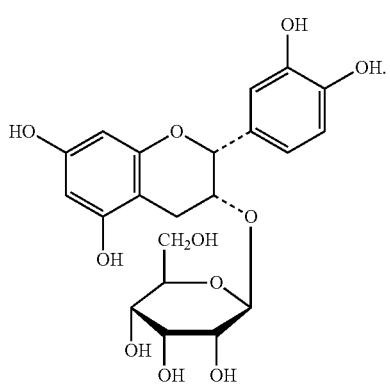

The result of the $^{13}$C- and $^1$H-NMR spectrum (200 MHz, CDCl3) of the compound of formula I is shown in TABLE 1.

TABLE 1

The $^{13}$C- and $^1$H-NMR spectrum of the compound of formula I

| C | | H | |
|---|---|---|---|
| C-2 | 79.19 | H-2 | 5.05 (d, J = 2.2 Hz) |
| C-3 | 73.40 | H-3 | 4.43 (m) |
| C-4 | 24.75 | H-4-2 | 2.74, 2.72 |
| C-5 | 157.85 | — | — |
| C-6 | 96.43 | H-6 | 5.86 (d, J = 2.3 Hz) |
| C-7 | 157.13 | — | — |
| C-8 | 95.68 | H-8 | 5.90 (d, J = 2.3 Hz) |
| C-9 | 157.13 | — | — |
| C-10 | 100.21 | — | — |
| C-1' | 131.67 | — | — |
| C-2' | 115.57 | H-2' | 7.02 (d, J = 2.1 Hz) |
| C-3' | 145.50 | — | — |
| C-4' | 145.72 | — | — |
| C-5' | 116.29 | H-5' | 6.66 (d, J = 8.2 Hz) |
| C-6' | 120.34 | H-6' | 6.78 (d, J = 2.1 Hz) |
| | | Allosyl | |
| C-1" | 100.41 | H-11' | — |
| C-2" | 72.28 | (H-2"-6") | — |
| C-3" | 72.91 | (H-5) | |
| C-4" | 68.96 | | |
| C-5" | 75.33 | | 4.74 (d, J = 8 Hz) |
| C-6" | 63.26 | | 3.22-3.99 |

Animal Study

The following experiment was performed and approved by the guidelines of the Institutional Animal Care and Use Committee of Central Taiwan University of Science and Technology. The 4-week old male C57BL/6J mice (total amount n=63) were purchased from the National Laboratory Animal Breeding and Research Center (Taipei, Taiwan). After acclimatization for one week, all of the mice were divided randomly into the control (CON) group and the high-fat diet (HFD) group. For the following 12 weeks, the CON group (n=9) was kept on a low-fat diet (Diet 12450B, Research Diets, Inc., New Brunswick, N.J., USA), while the HFD group (n=54) was exposed to a high-fat diet (Diet 12451, Research Diets, New Brunswick, N.J., USA). The low-fat diet was composed of protein 20%, carbohydrate 70% and fat 10%, whereas the high-fat diet was composed of protein 20%, carbohydrate 35%, and fat 45% (of total energy, % kcal). After HFD exposure for 8 weeks, the HFD group was further randomly subdivided into 6 groups (n=9 per group) to receive different treatments by oral gavage once daily for four weeks and on HFD. The 6 groups are the HF+B1 group (dosing of the compound of formula I at 10 mg/kg body wt/day), the HF+B2 group (dosing of the compound of formula I at 20 mg/kg body wt/day), the HF+B3 group (dosing of the compound of formula I at 40 mg/kg body wt/day), the HF+Rosi group (dosing of rosiglitazone (GlaxoSmithKline) at 10 mg/kg body wt/day in 1% methylcellulose), the HF+Feno group (dosing of fenofibrate (Sigma Chemical Co, St. Louis, Mich., USA) at 250 mg/kg body wt/day), and the HF group which was given vehicle (equal volumes of water). The HF+B1, HF+B2, and HF+B2 groups are collectively termed BB-treated HFD groups in the following examples. The CON mice were administered vehicle. After dosing for 4 weeks, the mice were given no food at night and sacrificed after 12 h of fasting on the next day. All of the individual tissues were collected and weighed, and portions were instantly frozen using liquid nitrogen and kept at −80° C. for subsequent target gene analysis. Blood samples (0.8 mL) were collected for analysis of blood parameters.

Measurement of Body Weight, Body Weight Gain, and Diet Consumption

Body weight of each mouse was monitored and measured daily at the same time throughout the experimentation. The difference in body weight between two consecutive days is defined as body weight gain. The food pellets for mice were weighed and put into the food container. Unconsumed pellets of high-fat diet were discarded each day and fresh pellets of high-fat diet were provided to ensure food quality throughout the experimentation. The high-fat food pellets were stored at 4° C.

Analysis of Blood Glucose, Blood Lipid, Insulin, Leptin, and Adiponectin

A portion of the blood samples obtained from the retro-orbital sinus of fasted mice were immediately used to measure blood glucose levels using Sidekick glucose analyzer (YSI 1500, YSI Incorporated, Yellow Springs, USA) according to the glucose oxidase method. Heparin (30 units/mL, Sigma) was added into other portions of the blood samples. Plasma samples were collected from the blood samples by centrifugation at 1600 g for 15 minutes at 4° C. Concentrations of plasma triglycerides (TG), total cholesterol (TC), and free fatty acids (FFA) were determined using commercial assay kits according to the manufacturer's instructions (Triglycerides-E test, Cholesterol-E test, and FFA-C test, Wako Pure Chemical, Osaka, Japan). Plasma insulin, leptin, and adiponectin levels were assessed using commercial assay kits according to the manufacturer's instructions (mouse insulin ELISA kit, Mercodia, Uppsala, Sweden; mouse leptin ELISA kit, Morinaga, Yokohama, Japan; Mouse Adiponectin ELISA kit, Crystal Chem International, Downers Grove, Ill., USA).

Analysis of Hepatic Lipids

For hepatic lipid extraction, a 0.375 g liver samples were homogenized with 1 mL distill water for 5 minutes. The dried pellet was finally resuspended in 0.5 mL ethanol and analyzed using a triglycerides kit as used for analyzing the serum lipids set forth above.

Histology of Adipose and Liver Tissue

Small pieces of epididymal white adipose tissue and liver tissue were fixed with formalin (200 g/kg) neutral buffered solution and embedded in paraffin. Sections of 8 μm in diameter were cut and stained with hematoxylin and eosin. For microscopic examination, a microscope (Leica, DM2500) was used, and the images were taken using a Leica Digital Camera (DFC-425-C).

Isolation of RNA

Total RNA from liver tissue of mice was isolated with a Trizol Reagent (Molecular Research Center, Inc., Cincinnati, Ohio, USA) according to the manufacturer's instructions. The integrity of the extracted total RNA was examined by 2% agarose gel electrophoresis, and the RNA concentration was determined by the ultraviolet (UV) light absorbency at 260 nm and 280 nm (Spectrophotometer U-2800A, Hitachi). The quality of the RNA was confirmed by ethidium bromide staining of 18S and 28S ribosomal RNA after electrophoresis on 2% agarose gel containing 6% formaldehyde.

Relative Quantization of mRNA

Levels of mRNA of genes of interest were quantified by semi-quantitative reverse transcription polymerase chain reaction (RT-PCR). The isolated total RNA (1 μg) was reverse transcribed to cDNA in a reaction mixture containing buffer, 2.5 mM dNTP (Gibco-BRL, Grand Island, N.Y.), 1 mM oligo (dT) primer, 50 mM dithiothreitol, 40 U Rnase inhibitor (Gibco-BRL, Grand Island, N.Y.), and 5 μL Moloney murine leukemia virus reverse transcriptase (TEpicentre, Madison, Wis., USA) at 37° C. for 1 hour and then heated at 90° C. for 5 minutes to terminate the reaction. The PCR was performed in a final 25 μL containing 1 U Blend Taq-Plus (TOYOBO, Japan), 10 μL of the RT cDNA product, 10 μM of each forward (F) and reverse (R) primer, 75 mM Tris-HCL (pH 8.3) containing 1 mg/L Tween 20, 25 mM dNTP, and 2 mM $MgCl_2$. Preliminary experiments were carried out with various cycles to determine the nonsaturating conditions of the PCR amplification for all the genes studied. The primers used are shown in TABLE 2. PCR products were analyzed by 2% agarose gels and stained with ethidium bromide. The relative intensity of each band was evaluated using AlphaDigiDoc 1201 software (Alpha Innotech Co., San Leandro, Calif., USA) and normalized to the band intensity of GAPDH in each sample.

TABLE 2

Primers used in PCR amplification

| Gene | Accession Numbers | Forward Primer and Reverse Primer | PCR Product (bp) | Annealing Temperature (° C.) |
|---|---|---|---|---|
| Liver | | | | |
| PEPCK | NM_011044.2 | F: CTACAACTTCGGCAAATACC (SEQ ID NO: 1)<br>R: TCCAGATACCTGTCGATCTC (SEQ ID NO: 2) | 330 | 52 |
| G6Pase | NM_008061.3 | F: GAACAACTAAAGCCTCTGAAAC (SEQ ID NO: 3)<br>R: TTGCTCGATACATAAAACACTC (SEQ ID NO: 4) | 350 | 50 |
| 11β-HSD1 | NM_008288.2 | F: AAGCAGAGCAATGGCAGCAT (SEQ ID NO: 5)<br>R: GAGCAATCATAGGCTGGGTCA (SEQ ID NO: 6) | 300 | 50 |
| Adiponectin | NM_009605.4 | F: TCTTCTACAACCAACAGAATCA (SEQ ID NO: 7)<br>R: GTATCATGGTAGAGAAGGAAGC (SEQ ID NO: 8) | 324 | 50.5 |
| PPARα | NM_011144 | F: CCTGAGATTAACCAGCCTTT (SEQ ID NO: 9)<br>R: AGGACCTACTCTCATTGCTG (SEQ ID NO: 10) | 352 | 55 |
| GPAT | BC019201.1 | F: CAGTCCTGAATAAGAGGT (SEQ ID NO: 11)<br>R: TGGACAAAGATGGCAGCAGA (SEQ ID NO: 12) | 441 | 48 |
| GAPDH | NM_008084.3 | F: TGTGTCCGTCGTGGATCTGA (SEQ ID NO: 13)<br>R: CCTGCTTCACCACCTTCTTGA (SEQ ID NO: 14) | 99 | 55 |

Western Immunoblotting Analysis

Protein extractions and immunoblots for the determination of phospho-AMPK (Thr$^{172}$) and phospho-Akt (Ser$^{473}$) proteins in skeletal muscle and liver tissue of mice (n=9) were carried out. About 0.1 g of liver tissue and skeletal muscle was used for the homogenate samples. Samples were powdered under liquid nitrogen and homogenized for 20 seconds in 500 μL buffer containing 20 mM Tris-HCL1 (pH 7.4 at 4° C.), 2% SDS, 5 mM EDTA, 5 mM EGTA, 1 mM DTT, 100 mM NaF, 2 mM sodium vanadate, 0.5 mM phenylmethylsulfonyl fluoride, 10 μg/mL leupeptin, and 10 μL/mL pepstatin. The protein concentration in supernatant was determined with a BCA protein assay kit (Thermo Scientific, Rockford, Ill., USA). 20 μg of proteins were separated by electrophoresis on a polyacrylamide gel 12% (SDS-PAGE) and transferred to a nitrocellulose membrane. The membranes were blocked with 5% slim milk in Tris-buffered saline (TBS)(Amersham BioSciences, Uppsala, Sweden) containing 0.05% Tween-20 (Bio Rad, CA, USA) and incubated overnight at 4° C. with anti-phospho-AMPK (Abcam Inc., Cambridge, Mass., USA) and anti-phospho-Akt (Cell signaling Technology, Inc., Danvers, Mass., USA) rabbit polyclonal antibodies at 1:200 dilution. Subsequently, the membranes were washed three times with TBS containing 0.05% Tween-20 and incubated with secondary antibody anti-rabbit (1:1000) (Jackson ImmunoResearch Laboratories, Inc., PA, USA) for 1 hour. Immunoreactive bands were detected with ECL reagent kit (GE Healthcare BioSciences, Buckinghamshire, UK). The intensity of blotting was analyzed using Alpha Easy FC software (Alpha Innotech Corporation, Randburg, South Africa). Structural proteins GAPDH (Santa Cruz Biotechnology, CA, USA) in the samples were used as the loading control.

Statistical Analysis

All results were presented as the mean and standard error (SE). Moreover, variance of data was analyzed based on Dunnett's multiple range tests using SPSS software (SPSS Inc., Chicago, Ill., USA). $p<0.05$ is recognized as statistically significant.

Example 1

1.1 Reductions in Weights of Adipose Tissue

White adipose weight of mice for the HF group and the BB-treated HFD groups was examined to verify the visceral fat weight gain-reducing effect of the compound of formula I. As shown in FIG. 1A and TABLE 3, the mean weights of each group at the beginning are similar (18.86±0.12 g). After 8 weeks, the HFD group was treated with vehicle, rosiglitazone (Rosi), fenofibrate (Feno), or various amounts of the compound of formula I as previously described and fed on HFD for additional 4 weeks. After 12 weeks, mice on HFD all exhibited increased body weight and body weight gain compared with the CON group. In FIG. 1A, all values are means±S. E. (n=9); the alphabet letters a, b, and c represent respectively $p<0.05$, $p<0.01$, and $p<0.001$ compared with the CON group. No significant difference was observed in body weight when a comparison was made between the HF group and either one of the HF+B1, HF+B2, HF+B3, HF+Rosi, and HF+Feno groups. However, the HF+B3 group and the HF+Feno group displayed reduced weight gain compared with the HF group. The HFD group consumes a HFD (g) much less than the CON group ($p<0.001$). Food intake of the HF+B1, HF+B2, HF+B3, HF+Rosi, and HF+Feno groups was similar to the HF group.

According to TABLE 3, the HF group displayed increased weights of epididymal white adipose tissue (EWAT), retro-peritoneal WAT (RWAT), visceral fat, mesenteric WAT (MWAT), skeletal muscle, and brown adipose tissue (BAT) compared with the CON group. However, all of the HF+B1, HF+B2, HF+B3, HF+Rosi, and HF+Feno groups showed reduced EWAT, RWAT, and visceral fat weights. The HF+B3 group exhibited increased skeletal muscle weights ($p<0.05$) while the HF+Feno group displayed increased liver weight. These results indicate that the compound of formula I of the present invention significantly reduces weights of adipose tissue and visceral fat.

TABLE 3

Effects of the compound of formula I on absolute tissue weight, body weight gain, food intake, liver lipids, and blood parameters

| Parameter | CON | HF | HF + B1 | HF + B2 | HF + B3 | HF + Rosi | HF + Feno |
|---|---|---|---|---|---|---|---|
| Dose (mg/kg/day) | 0 | 0 | 10 | 20 | 40 | 10 | 250 |
| Absolute tissue weight (g) | | | | | | | |
| EWAT | 0.415 ± 0.029 | 1.303 ± 0.123$^c$ | 0.906 ± 0.105$^d$ | 0.902 ± 0.084$^d$ | 0.936 ± 0.075$^d$ | 0.919 ± 0.097$^d$ | 0.763 ± 0.116$^f$ |
| MWAT | 0.139 ± 0.024 | 0.310 ± 0.027$^b$ | 0.293 ± 0.018 | 0.267 ± 0.021 | 0.236 ± 0.030 | 0.302 ± 0.029 | 0.264 ± 0.056 |
| RWAT | 0.089 ± 0.012 | 0.469 ± 0.057$^c$ | 0.280 ± 0.043$^d$ | 0.263 ± 0.034$^f$ | 0.233 ± 0.026$^f$ | 0.224 ± 0.032$^f$ | 0.173 ± 0.032$^f$ |
| Visceral fat | 0.504 ± 0.039 | 1.772 ± 0.173$^c$ | 1.273 ± 0.147$^d$ | 1.199 ± 0.104$^e$ | 1.198 ± 0.075$^e$ | 1.143 ± 0.124$^e$ | 0.936 ± 0.147$^f$ |
| Skeletal muscle | 0.662 ± 0.036 | 0.874 ± 0.078$^a$ | 0.873 ± 0.060 | 0.813 ± 0.077 | 1.156 ± 0.102$^d$ | 0.960 ± 0.078 | 0.990 ± 0.078 |
| BAT | 0.084 ± 0.008 | 0.171 ± 0.014$^b$ | 0.168 ± 0.011 | 0.156 ± 0.017 | 0.144 ± 0.010 | 0.206 ± 0.012 | 0.139 ± 0.011 |
| Liver (g) | 0.879 ± 0.019 | 0.884 ± 0.035 | 0.899 ± 0.036 | 0.866 ± 0.038 | 0.848 ± 0.028 | 0.886 ± 0.031 | 1.669 ± 0.033$^f$ |
| Weight gain (g) | 0.01 ± 0.19 | 0.89 ± 0.16$^a$ | 0.40 ± 0.28 | 0.61 ± 0.43 | −0.05 ± 0.11$^d$ | 0.38 ± 0.32 | −0.58 ± 0.48$^d$ |
| Body weight (g) | 24.37 ± 0.46 | 28.80 ± 0.93$^b$ | 27.85 ± 1.04 | 27.88 ± 1.14 | 27.15 ± 0.84 | 28.61 ± 1.51 | 26.92 ± 0.96 |
| Food intake (g/day/mouse) | 2.40 ± 0.04 | 2.14 ± 0.04$^c$ | 2.08 ± 0.05 | 2.03 ± 0.03 | 2.02 ± 0.03 | 2.11 ± 0.06 | 2.14 ± 0.04 |
| Liver lipids | | | | | | | |
| Total lipid (mg/g) | 55.3 ± 4.5 | 99.1 ± 7.1$^b$ | 71.9 ± 6.5$^d$ | 66.1 ± 6.9$^e$ | 60.2 ± 5.2$^f$ | 70.1 ± 8.2$^d$ | 62.4 ± 3.9$^f$ |
| Triacylglycerol (μmol/g) | 42.1 ± 4.5 | 81.1 ± 7.8$^b$ | 49.9 ± 8.0$^d$ | 42.8 ± 6.5$^f$ | 40.8 ± 4.6$^f$ | 52.1 ± 7.7$^d$ | 43.8 ± 5.6$^f$ |
| Blood parameters | | | | | | | |
| FFA (mEq/L) | 1.02 ± 0.10 | 1.48 ± 0.23$^b$ | 1.11 ± 0.13$^d$ | 0.95 ± 0.04$^f$ | 0.86 ± 0.09$^f$ | 1.08 ± 0.11$^e$ | 0.91 ± 0.08$^f$ |
| TC (mg/dL) | 104.6 ± 8.6 | 163.8 ± 7.2$^c$ | 153.5 ± 7.7 | 144.1 ± 4.0 | 142.9 ± 6.6 | 111.5 ± 2.3$^f$ | 104.5 ± 5.5$^f$ |
| Leptin (ng/mL) | 1.359 ± 0.044 | 2.133 ± 0.044$^c$ | 1.662 ± 0.009$^f$ | 1.372 ± 0.029$^f$ | 1.321 ± 0.008$^f$ | 1.661 ± 0.013$^f$ | 1.206 ± 0.015$^f$ |

TABLE 3-continued

Effects of the compound of formula I on absolute tissue weight, body weight gain, food intake, liver lipids, and blood parameters

| Parameter | CON | HF | HF + B1 | HF + B2 | HF + B3 | HF + Rosi | HF + Feno |
|---|---|---|---|---|---|---|---|
| Adiponectin (μg/mL) | 2.737 ± 0.021 | 2.153 ± 0.036[c] | 2.895 ± 0.010[f] | 3.277 ± 0.052[f] | 3.628 ± 0.034[f] | 3.058 ± 0.040[f] | 3.101 ± 0.028[f] |

All values are means ± S.E. (n = 9);
[a] $p < 0.05$,
[b] $p < 0.01$,
[c] $p < 0.001$ compared with the CON group;
[d] $p < 0.05$,
[e] $p < 0.01$,
[f] $p < 0.001$ compared with the HF group.

1.2 Reductions in Blood Levels of Glucose and Insulin

Figure 1B:
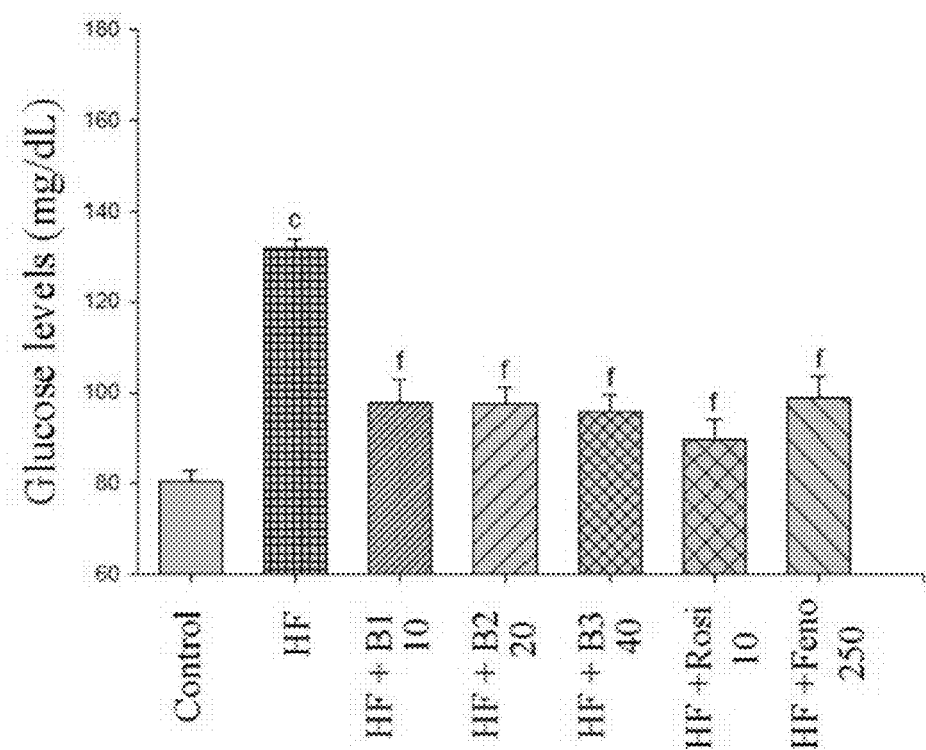
FIG. 1B shows the effect of the compound of formula I on blood glucose levels.
Figure 1C:
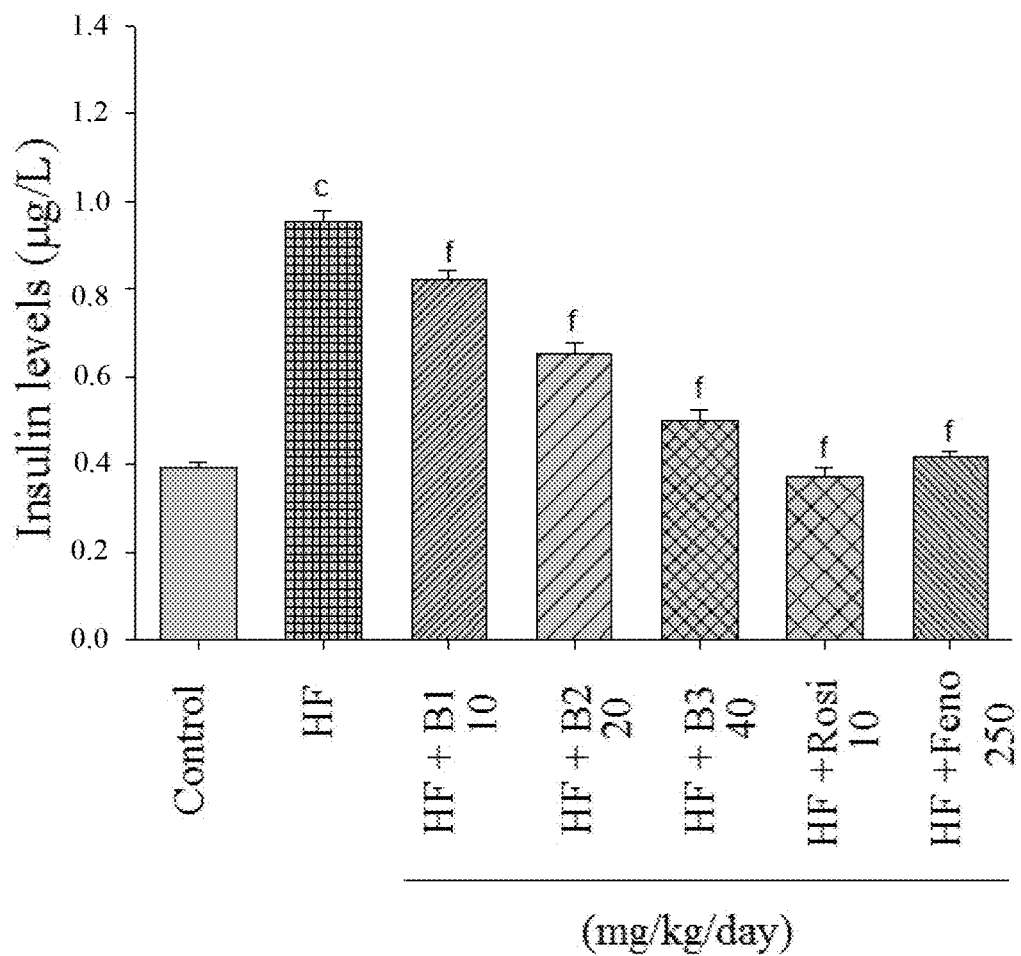
FIG. 1C shows the effect of the compound of formula I on blood insulin levels.

Levels of glucose and insulin in blood for the HF group and the BB-treated HFD groups were examined to verify the glucose- and insulin-lowering effects of the compound of formula I. As shown in FIG. 1B and FIG. 1C, when compared with the CON group, the HF group showed evidence of hyperglycemia and hyperinsulinemia after 12 weeks on HFD exposure. However, the HF+B1, HF+B2, HF+B3, HF+Rosi, and HF+Feno groups exhibited markedly lowered blood levels of glucose and insulin. In FIGS. 1B-1C, all values are means±S. E. (n=9); the alphabet letters c and f represent respectively $p<0.001$ compared with the CON group and $p<0.001$ compared with the HF group. These results indicate that the compound of formula I of the present invention significantly reduces blood levels of glucose and insulin.

Figure 1D:
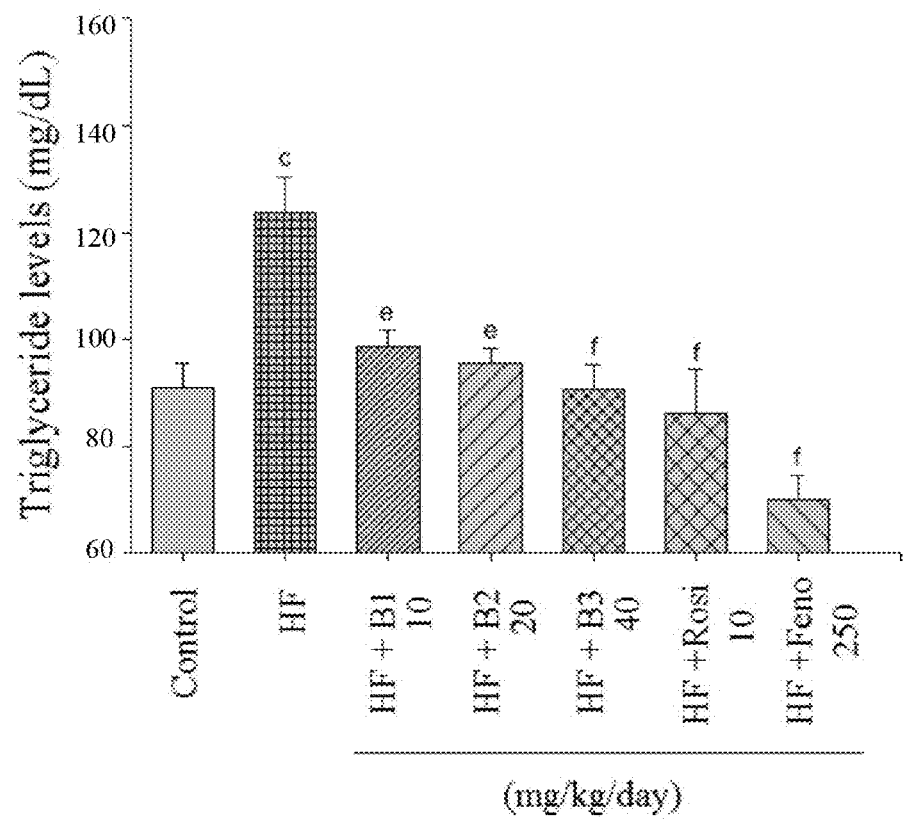
FIG. 1D shows the effect of the compound of formula I on triglyceride levels.

1.3 Reductions in Blood Levels of Triglycerides, Free Fatty Acids, and Leptin and Hepatic Levels of Total Lipid and Triacylglycerol Levels of lipid and leptin in blood and hepatic lipid for the HF group and the BB-treated HFD groups were examined to verify the lipid-lowering effect of the compound of formula I. As shown in FIG. 1D and TABLE 3, when compared with the CON group, the HF group had enhanced circulating levels of triglycerides (TG), total cholesterol (TC), leptin, and free fatty acid (FFA) after 12 weeks on HFD exposure, whereas there were decreased adiponectin levels, which indicated an inverse correlation between adiponectin and blood lipid. Administration of the compound of formula I, Rosi, and Feno decreased TG and FFA levels. The HF+Rosi and HF+Feno groups had lower TC levels. In addition, the HF+B1, HF+B2, HF+B3, HF+Rosi, and HF+Feno groups displayed reduced blood concentrations of leptin, whereas they had enhanced blood levels of adiponectin. In FIG. 1D, all values are means±S. E. (n=9); the alphabet letter c represents $p<0.001$ compared with the CON group, and the letters e and f represent respectively $p<0.01$ and $p<0.001$ compared with the HF group.

In liver tissues, not only total lipid but also triacylglycerol levels were enhanced in the HF group compared with the CON group. Administration of the indicated amounts of the compound of formula I, Rosi, and Feno decreased total lipid and triacylglycerol in the liver. These results indicate that the compound of formula I of the present invention reduces blood levels of triglycerides, free fatty acids, and leptin and hepatic levels of total lipid and triacylglycerol, while it increases the blood level of adiponectin.

Example 2

Inhibition of Adipocyte Hypertrophy

Adipocyte hypertrophy, the pathological enlargement of adipocytes, is often found in subjects with type 2 diabetes and hyperlipidemia. To verify the therapeutic effect of the compound of formula I on adipocyte hypertrophy, morphology of the EWAT for the CON group and the BB-treated HFD groups was examined. Micrographs of the EWAT sections for each group were analyzed to determine the mean area of an epididymal adipocyte using the software ImageJ.

Figure 2:
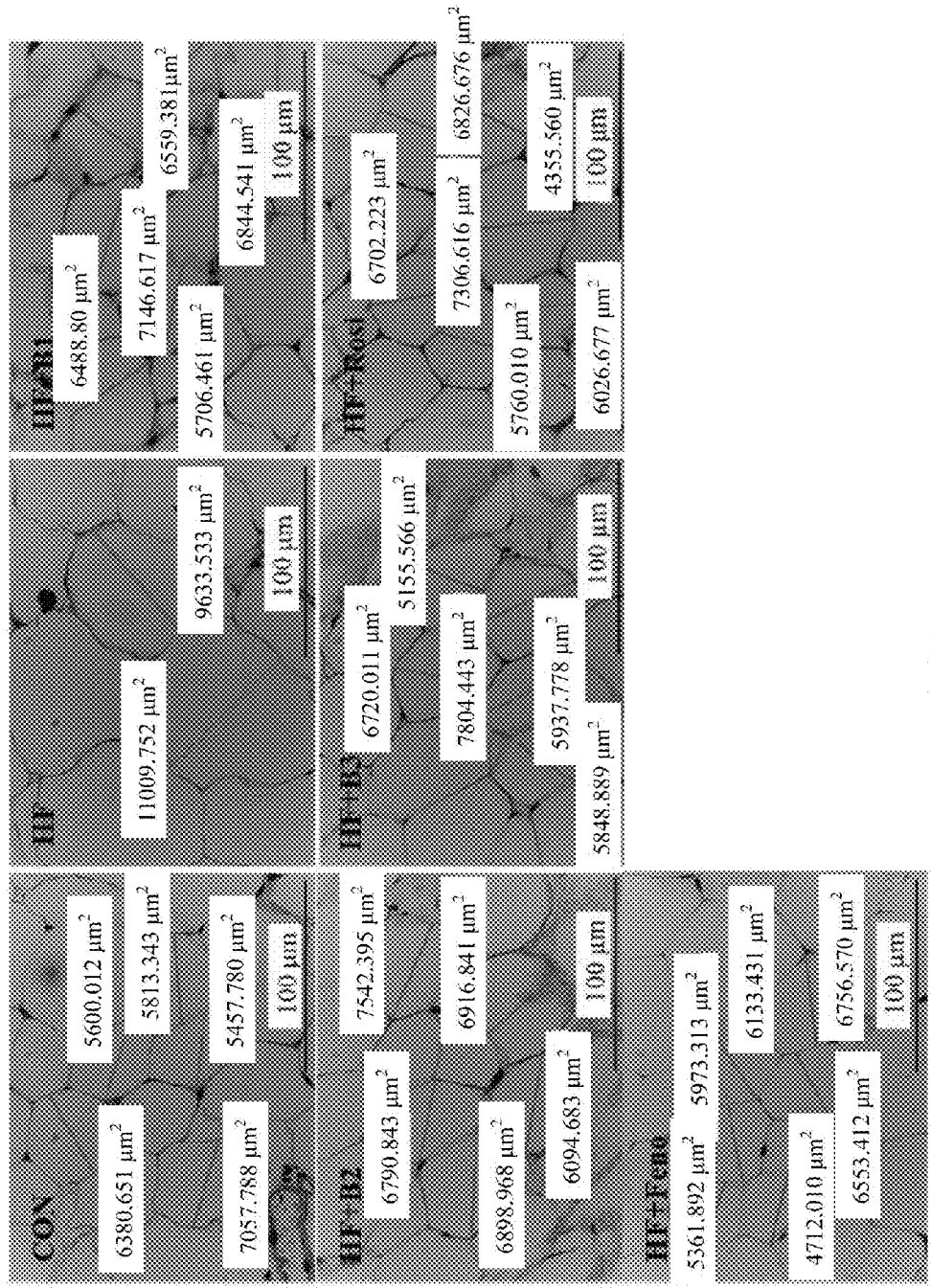
FIG. 2 shows micrographs (magnification: 200×) of adipocytes from the epididymal white adipose tissue of mice with or without treatment of the compound of formula I and the area ($\mu^2$) of adipocytes.

As shown in FIG. 2, the HF group was characterized by adipocyte hypertrophy when compared with the CON group. The mean area of an epididymal adipocyte for the HF group was 10216.4±338.4 μm$^2$ while that for the CON group was 5347.5±408.9 μm$^2$. However, the HF+B1, HF+B2, HF+B3, HF+Rosi, and HF+Feno groups displayed significant resistant to hypertrophy, each of which showed the mean adipocyte areas of 6882.8±102.2 μm$^2$, 6475.5±102.6 μm$^2$, 6192.7±100.7 μm$^2$, 5886.4±58.7 μm$^2$, and 6982.3±309.7 μm$^2$, respectively. All values were calculated based on three measurements. These data indicate that the compound of formula I of the present invention inhibits adipocyte hypertrophy.

Example 3

Decrease in Hepatocellular Ballooning

Hepatocellular ballooning, which is resulted from hepatocyte death and accumulated glycan in the cell, is usually observed in type 2 diabetes- and hyperlipidemia-related fatty liver. To further validate the therapeutic effect of the compound of formula I on hepatocellular ballooning, morphology of the liver tissue for the CON group and the BB-treated HFD groups was examined.

Figure 3:
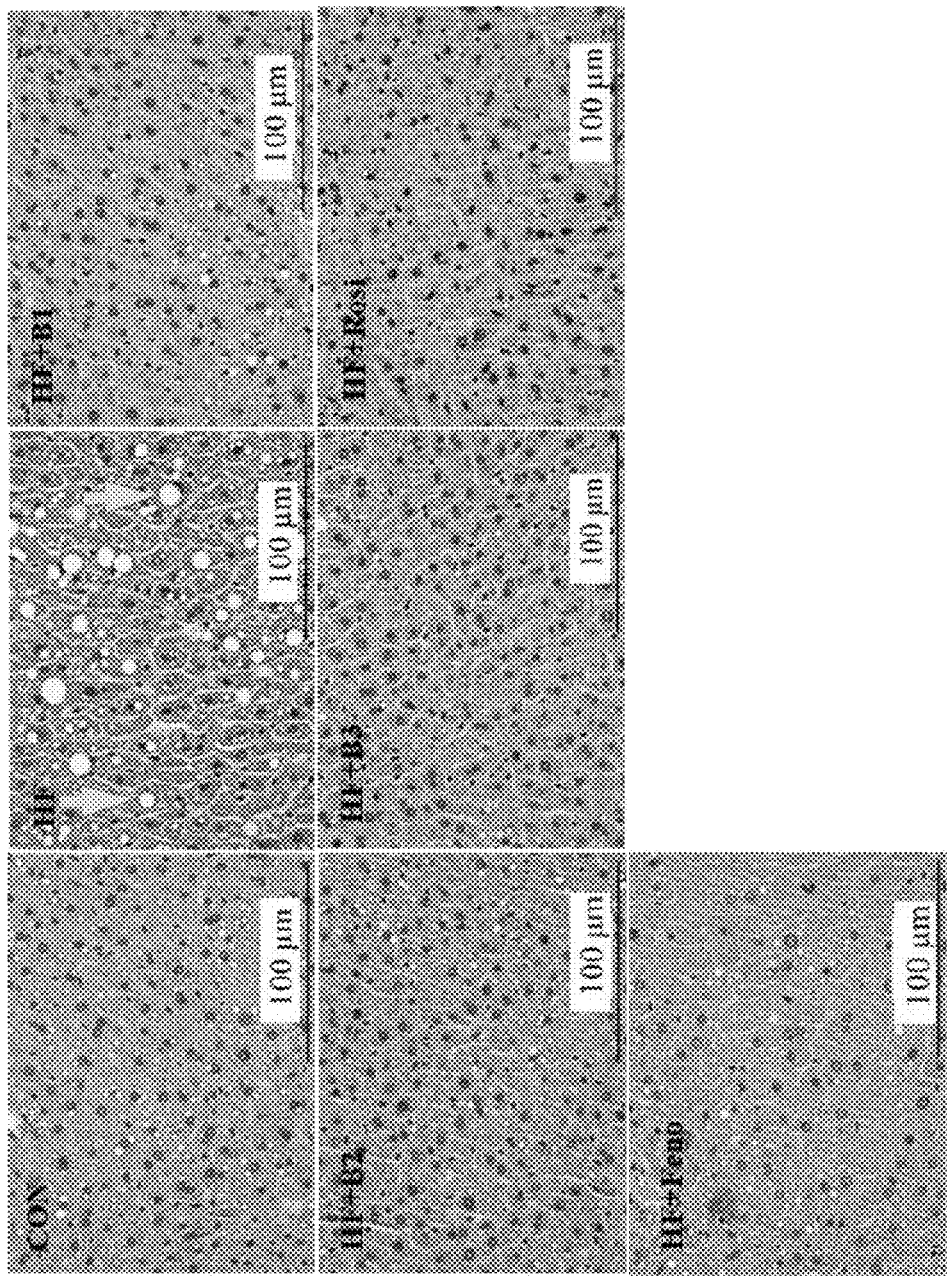
FIG. 3 shows micrographs (magnification: 200×) of liver tissue ($\mu m^2$) of mice with or without treatment of the compound of formula I.

As shown in FIG. 3, when compared with the CON group, the liver of the HF group displayed significant ballooning degeneration of hepatocytes, with the nucleolus being squeezed into the side, which is the so-called ballooning (indicated by white arrow in FIG. 3). Based on previous report, the designation of histological hepatocellular ballooning findings include grade 0 for absence of degeneration, grade 1 for degeneration in a few cells, and grade 3 for degeneration in many cells. While HFD caused ballooning (mean score=1.9±0.2), the appearance of ballooning was less in the HF+B1 (0.7±0.1), HF+B2 (0.5±0.2), HF+B3 (0.4±0.1), HF+Rosi (0.8±0.2), and HF+Feno (0.6±0.1) groups. These data indicate that the compound of formula I of the present invention decreases the degree of hepatocellular ballooning.

Example 4

Regulation of mRNA Expression of the Hepatic Genes Related to Glucose Production and Lipid Synthesis Change in protein expression of several enzymes essential in glucose and lipid metabolism was studied. Phosphenolpyruvate carboxykinase (PEPCK) and glucose-6-phosphatase (G6Pase) are the rate-limiting enzymes in gluconeogenesis. 11β hydroxysteroid dehydrogenase 1 (11-β-HSD1) knockout has been reported to ameliorate insulin resistance. Diacylglycerol acyltransferase (DGAT2) and glycerol-3-phosphate-acyltransferase (GPAT) are enzymes participating in glycerolipid biosynthesis. PPARα are associated with fatty acid oxidation in liver. Adipoectin in blood has been reported to be decreased in type 2 diabetes and obesity and raise liver insulin sensitivity. To investigate the effects of the compound of formula I on gene expression of PEPCK, G6Pase, 11β-HSD1, adiponectin, PPARα, DGAT2, and GPAT in liver, quantification of the mRNA levels of these proteins was performed for the CON group and the BB-treated HFD groups.

Figure 4A:
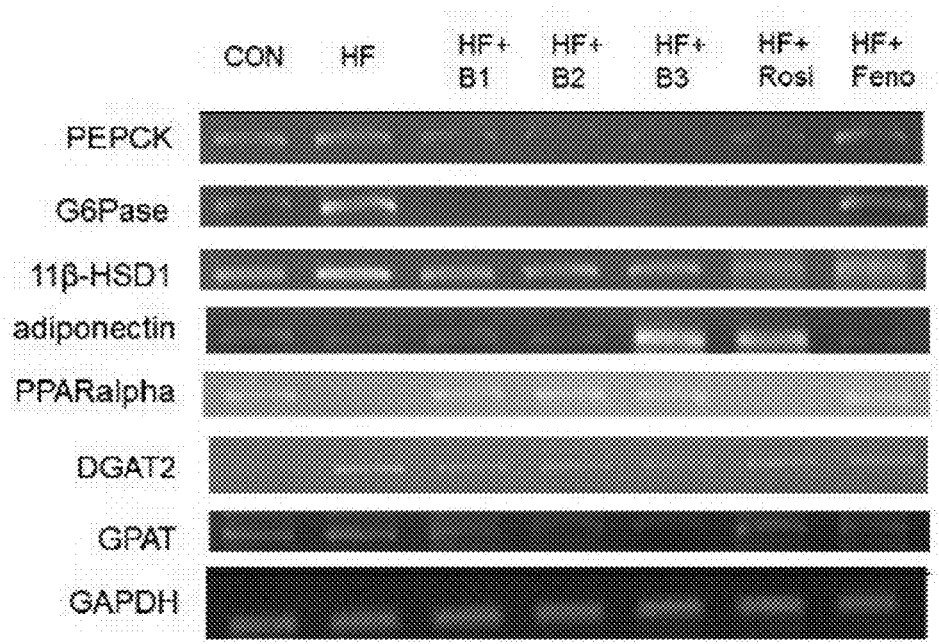
FIG. 4A shows gel image of electrophoresis for semi-quantitive RT-PCR analysis on phosphenolpyruvate carboxykinase (PEPCK), glucose-6-phosphatase (G6Pase), 11β hydroxysteroid dehydrogenase 1 (11-β-HSD1), adiponectin, PPARα, diacylglycerol acyltransferase (DGAT2), and glycerol-3-phosphate-acyltransferase (GPAT) mRNA expression in liver tissue of mice with or without treatment of the compound of formula I.
Figure 4B:
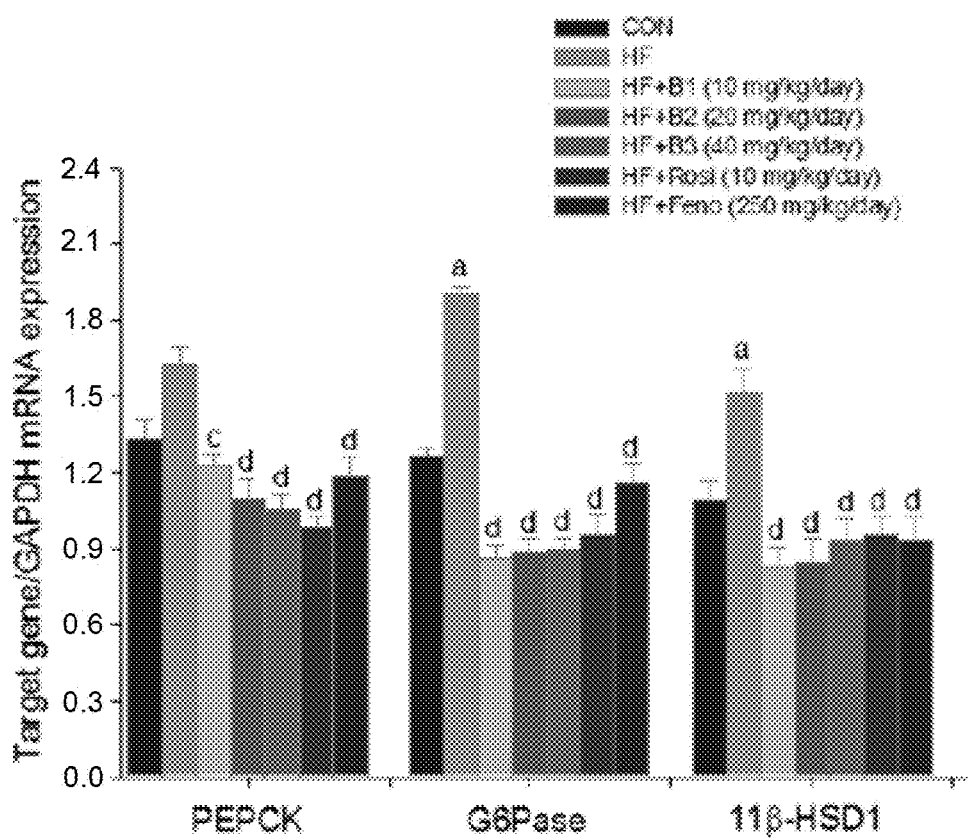
FIG. 4B shows target gene/GADPH mRNA expression levels of PEPCK, G6Pase, and 11β-HSD1 in liver tissue of mice with or without treatment of the compound of formula I.
Figure 4C:
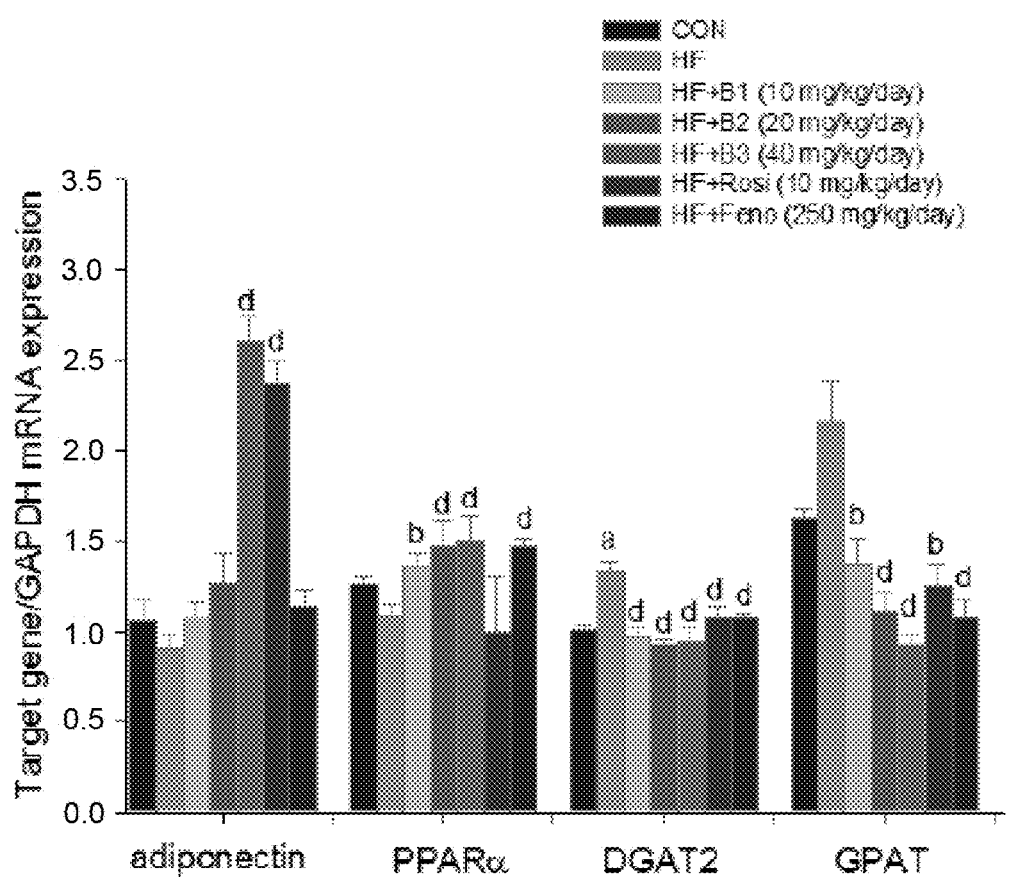
FIG. 4C shows target gene/GADPH mRNA expression levels of adiponectin, PPARα, DGAT2, and GPAT in liver tissue of mice with or without treatment of the compound of formula I.

As shown in FIGS. 4A-4C, the HF group had higher mRNA levels of G6Pase and 11β-HSD1 than the CON group after 12 weeks, while the HF+B1, HF+B2, HF+B3, HF+Rosi, and HF+Feno groups had significantly reduced mRNA levels of PEPCK, G6Pase, 11β-HSD1, DGAT2, and GPAT. However, the HF+B1, HF+B2, HF+B3, and HF+Feno groups showed enhanced PPARα mRNA levels. The HF+B3 and HF+Rosi group also had enhanced adiponectin mRNA levels. In FIGS. 4B-4C, all values are means±S. E. (n=9); the alphabet letter a represents $p<0.001$ compared with the CON group, and the letters b, c, and d represent respectively $p<0.05$, $p<0.01$, and $p<0.001$ compared with the HF group. These results indicate that the compound of formula I of the present invention inhibits expression of genes related to hepatic glucose production, such as PEPCK and G6Pase, and genes related to lipogenesis, such as 11β-HSD1, DGAT2, and GPAT. The results also show that the compound of formula I promotes expression of genes contributing to enhanced insulin sensitivity, such as adiponectin, and increased fatty acid oxidation, such as and PPARα.

Example 5

Regulation of Protein Expression of GLUT4 at the Plasma Membrane and Protein Phosphorylation of AMPK and Akt in Liver and Skeletal Muscle GLUT4 expressed at the plasma membrane involves in glucose uptake in skeletal muscle and thus regulates glucose levels in blood. Protein kinase B (often termed Akt) has been reported to stimulate glucose uptake by influencing GLUT4 in skeletal muscle and contributes to suppression of gluconeogenesis in liver. AMPK regulates metabolism of glucose and lipid and its activity depends on phosphorylation of the amino acid residue Thr 172 of the a subunit. To analyze the effects of the compound of formula I on GLUT4 expression at the plasma membrane in skeletal muscle and Akt and AMPK phosphorylation in liver and skeletal muscle, western blotting of these proteins was performed for the CON group and the BB-treated HFD groups.

Figure 5A:
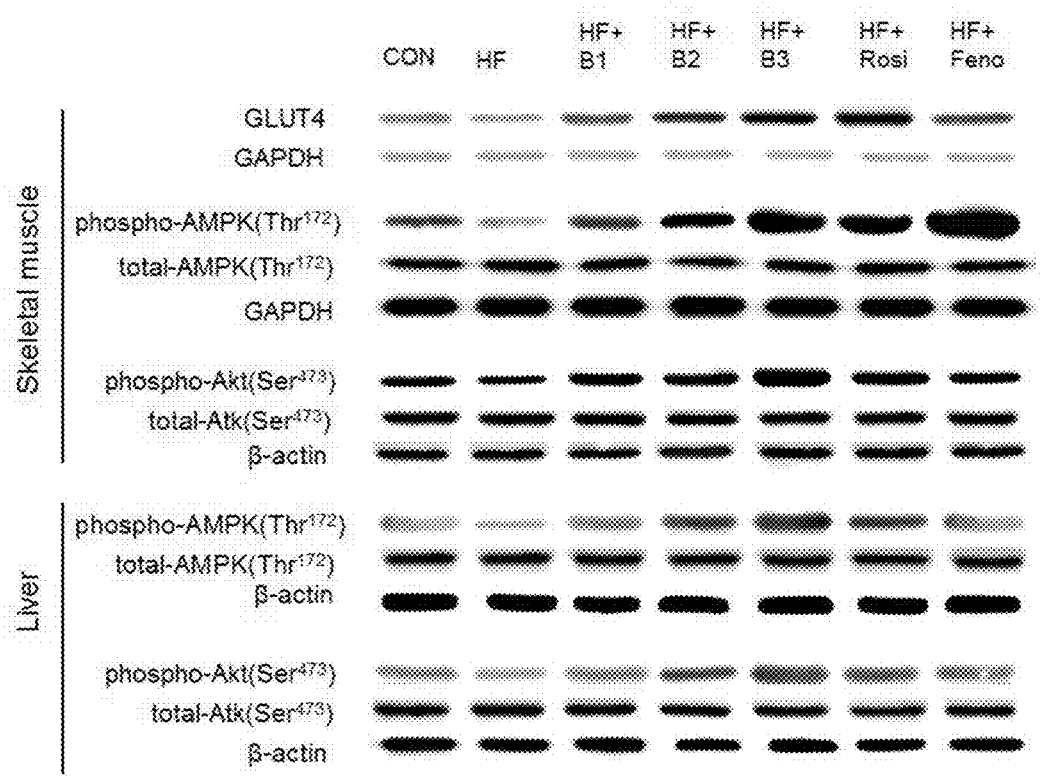
FIG. 5A shows image of western blotting of GLUT4 in skeletal muscle and phospho-AMPK, total AMPK, phospho-protein kinase B (often termed phospho-Akt), and total Akt in liver tissue and skeletal muscle of mice with or without treatment of the compound of formula I.
Figure 5B:
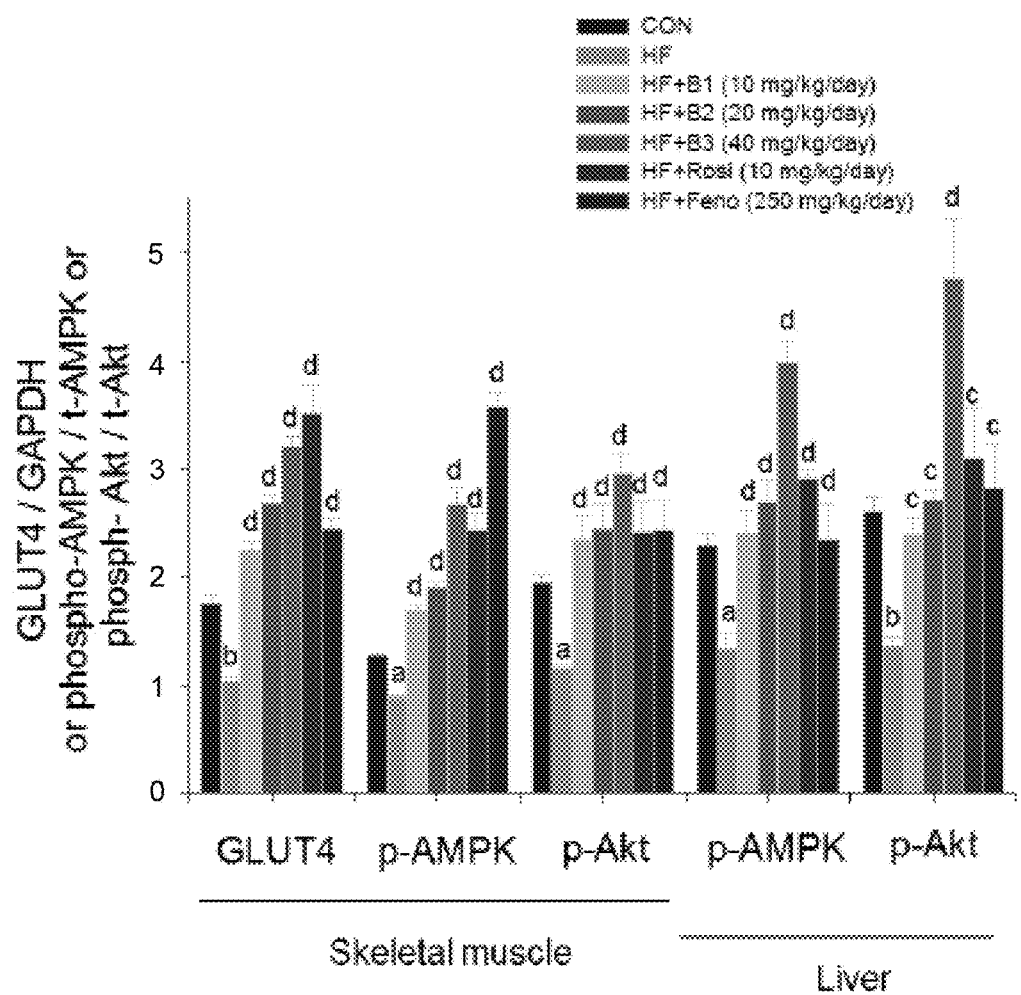
FIG. 5B shows protein expression levels of GLUT4/GAPDH in skeletal muscle and protein expression levels of phospho-AMPK/total AMPK and phospho-Akt/total Akt in liver tissue and skeletal muscle of mice with or without treatment of the compound of formula I.

As shown in FIGS. 5A-5B, the HF group had lower protein content of membrane GLUT4 in skeletal muscle than the CON group after 12 weeks, but the HF+B1, HF+B2, HF+B3, HF+Rosi, and HF+Feno groups had significantly enhanced protein levels of GLUT4 at the plasma membrane. The HF group also exhibited decreased expression levels of phospho-AMPK/total AMPK in both skeletal muscle and liver when compared with the CON group, while the HF+B1, HF+B2, HF+B3, HF+Rosi, and HF+Feno groups showed enhanced expression levels of phospho-AMPK/total AMPK in these two tissues. In addition, the HF group had lower expression levels of phospho-Akt/total Akt in both skeletal muscle and liver when compared with the CON group, while the HF+B1, HF+B2, HF+B3, HF+Rosi, and HF+Feno groups displayed increased expression levels of phospho-Akt/total Akt in both tissues. In FIG. 5B, all values are means±S. E. (n=9); the alphabet letters a and b represent respectively $p<0.05$ and $p<0.001$ compared with the CON group, and the letters c and d represent respectively $p<0.05$ and $p<0.001$ compared with the HF group. These results indicate that the compound of formula I of the present invention increases GLUT4 muscular expression and phosphorylation of Akt, which contributes to the effect of the compound of formula I in increasing insulin sensitivity and glucose uptake and leads to reductions in blood glucose levels. The results also indicate that the compound of formula I enhances phosphorylation of AMPK in skeletal muscle, which stimulates glucose transport, and this compound increases phosphorylation of AMPK in liver tissue, which contributes to inhibited hepatic glucose production through down-regulation of PEPCK and G6Pase and suppressed fatty acid synthesis through down-regulation of GPAT.

In conclusion, treatment of mice on HFD with the compound of formula I of the present invention caused significant reductions in weight of adipose tissue, such as EWAT and visceral fat, blood levels of triglycerides, free fatty acids, glucose, insulin, and leptin, and hepatic levels of total lipid and triacylglycerol. Treatment with the compound of formula I also significantly increases the adiponectin level in blood. Furthermore, the compound of formula I inhibits adipocyte hypertrophy and decreases the degree of ballooning degeneration in liver tissue. All the aforementioned antidiabetic and antihyperlipidemic effects may be interpreted as being resulted from the reduced mRNA expression of PEPCK, G6Pase, 11β-HSD1, DGAT2, and GPAT and the enhanced mRNA expression of PPARα and adiponectin in liver upon treatment with the compound of formula I. In addition, increased phosphorylation of AMPK and Akt in both liver and skeletal muscle may also contribute to the antidiabetic and antihyperlipidemic effects. Therefore, a method of treating or preventing type 2 diabetes and hyperlipidemia in a subject in need thereof can be developed by administrating to the subject a therapeutically effective amount of the compound of formula I of the present invention.

Besides, it is practicable to manufacture a pharmaceutical composition comprising the compound of formula I and a pharmaceutically acceptable carrier for treatment and prevention of type 2 diabetes and hyperlipidemia. The composition may further comprise an excipient, a diluent, a medium, or any combinations thereof. The compound of formula I can also be used in, for example, food supplements, for alleviating symptoms associated with type 2 diabetes and hyperlipidemia. These food supplements may further comprise an additive, such as a healthy food ingredient. The healthy food ingredients include but not limit to citric acid, taurine, vitamin, pantothenic acid, nicotinic acid, or any other edible substances that are beneficial to body health.

The method of treating or preventing type 2 diabetes and hyperlipidemia and the pharmaceutical composition performing the same provided in present invention is applicable and valuable to the industry. The present invention has been described with reference to the above preferred embodiments. However, it will be apparent to those skilled in the art that modifications and changes in form and detail may be made without departing from the scope of the present invention defined by the appended claims.

What is claimed is:

1. A method of treating type 2 diabetes and hyperlipidemia in a subject in need thereof, comprising administrating to the subject a therapeutically effective amount of a compound of formula I:

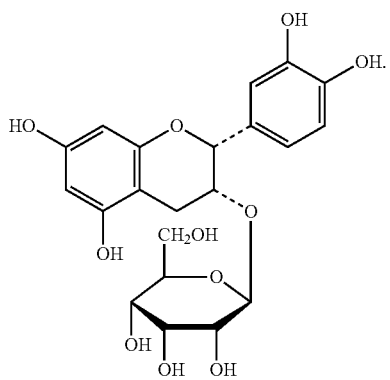

2. The method of claim 1, wherein the compound of formula I reduces a weight of visceral fat, a weight of epididymal white adipose tissue, and a weight of retroperitoneal white adipose tissue.

3. The method of claim 1, wherein the compound of formula I reduces a blood level of glucose.

4. The method of claim 1, wherein the compound of formula I reduces a blood level of insulin.

5. The method of claim 1, wherein the compound of formula I reduces a blood level of triglycerides and a blood level of free fatty acids.

6. The method of claim 1, wherein the compound of formula I reduces a blood level of leptin.

7. The method of claim 1, wherein the compound of formula I increases a blood level of adiponectin.

8. The method of claim 1, wherein the compound of formula I reduces a hepatic level of total lipid and a hepatic level of triacylglycerol.

9. The method of claim 1, wherein the compound of formula I inhibits hypertrophy of an adipocyte.

10. The method of claim 1, wherein the compound of formula I decreases hepatocellular ballooning.

11. The method of claim 1, wherein the compound of formula I inhibits gene expression of phosphenolpyruvate carboxykinase (PEPCK), glucose-6-phosphatase (G6Pase), 110 hydroxysteroid dehydrogenase 1 (11β-HSD1), diacylglycerol acyltransferase (DGAT2), and glycerol-3-phosphate-acyltransferase (GPAT) in liver.

12. The method of claim 1, wherein the compound of formula I enhances gene expression of peroxisome proliferator-activated receptor α (PPARα) and adiponectin in liver.

13. The method of claim 1, wherein the compound of formula I increases protein content of membrane glucose transporter type 4 (GLUT4) in skeletal muscle.

14. The method of claim 1, wherein the compound of formula I increases phosphorylation of 5' adenosine monophosphate-activated protein kinase (AMPK) and protein kinase B (Akt) in skeletal muscle and liver.

15. The method of claim 1, wherein the therapeutically effective amount is at least 10 mg/kg/day.

* * * * *